(12) United States Patent
Faber et al.

(10) Patent No.: US 8,854,738 B2
(45) Date of Patent: Oct. 7, 2014

(54) COUPLING DEVICE FOR DETACHABLY CONNECTING AN EYEPIECE OF AN ENDOSCOPE OPTICAL SYSTEM WITH A CAMERA LENS

(75) Inventors: Fredy Faber, Knittlingen (DE); Alexander Lampert, Ölbronn-Dürrn (DE); Andreas Michels, Walzbachtal (DE)

(73) Assignee: Richard Wolf GmbH, Knittlingen (DE)

( * ) Notice: Subject to any disclaimer, the term of this patent is extended or adjusted under 35 U.S.C. 154(b) by 190 days.

(21) Appl. No.: 13/171,539

(22) Filed: Jun. 29, 2011

(65) Prior Publication Data
US 2011/0317274 A1 Dec. 29, 2011

(30) Foreign Application Priority Data

Jun. 29, 2010 (DE) .......................... 10 2010 025 556

(51) Int. Cl.
*G02B 25/00* (2006.01)
*A61B 1/00* (2006.01)
*G03B 17/48* (2006.01)
*G02B 23/24* (2006.01)

(52) U.S. Cl.
CPC ......... *A61B 1/00126* (2013.01); *A61B 1/00195* (2013.01); *G03B 17/48* (2013.01); *G02B 23/2484* (2013.01); *A61B 1/00128* (2013.01)
USPC ........................................................ 359/643

(58) Field of Classification Search
CPC .......... G02B 25/00; G02B 23/14; G02B 7/02; G02B 7/00; G02B 5/00; G03B 17/14; A61B 1/05; A61B 1/04; A61B 1/06

USPC ........... 600/109, 112, 122; 352/131; 359/600, 359/827, 894, 643; 396/17
See application file for complete search history.

(56) References Cited

U.S. PATENT DOCUMENTS

| 4,182,558 A | * | 1/1980 | Matsuo ............................ 396/17 |
| 4,305,386 A | | 12/1981 | Tawara |
| 4,697,894 A | * | 10/1987 | Takamura et al. ............ 359/503 |
| 4,844,071 A | * | 7/1989 | Chen et al. ..................... 600/112 |
| 5,347,988 A | | 9/1994 | Hori |
| 6,468,202 B1 | * | 10/2002 | Irion et al. ..................... 600/117 |
| 6,494,826 B1 | | 12/2002 | Chatenever et al. |

FOREIGN PATENT DOCUMENTS

| DE | 6926837 U | 11/1969 |
| DE | 19712645 C1 | 10/1998 |
| DE | 19715510 A1 | 10/1998 |
| DE | 202008000449 U1 | 3/2008 |

OTHER PUBLICATIONS

Office Action issued Apr. 1, 2011 in DE Application No. 10 2010 025 556.4.

* cited by examiner

*Primary Examiner* — James Greece
*Assistant Examiner* — Jie Lei
(74) *Attorney, Agent, or Firm* — Panitch Schwarze Belisario & Nadel LLP

(57) ABSTRACT

A coupling device for detachably connecting an eyepiece of an endoscope optical system with a camera lens includes a receptacle for the eyepiece, attachment means for securing the eyepiece in the receptacle, and a manually activated handle arranged on the outside for releasing the attachment. The attachment means are controlled by the eyepiece so as to automatically attach the eyepiece in the receptacle while introducing the eyepiece into the receptacle.

11 Claims, 2 Drawing Sheets

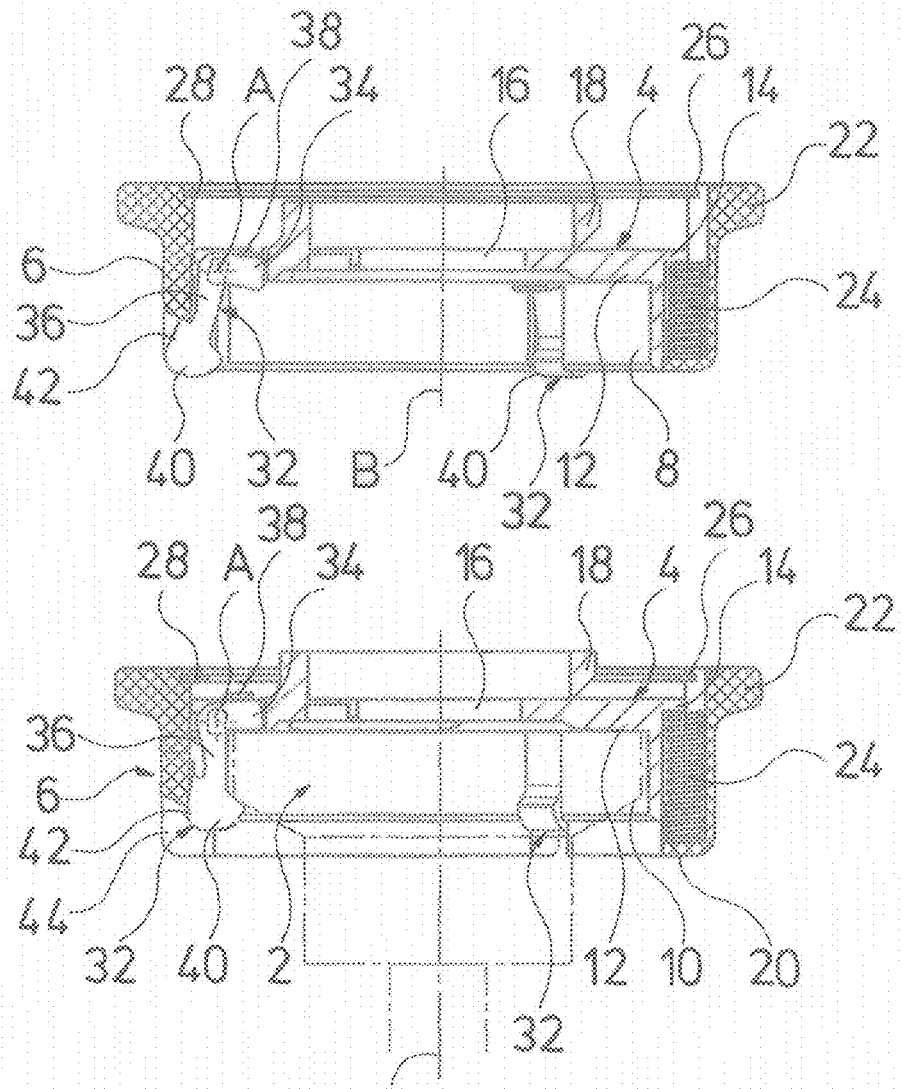

COUPLING DEVICE FOR DETACHABLY CONNECTING AN EYEPIECE OF AN ENDOSCOPE OPTICAL SYSTEM WITH A CAMERA LENS

BACKGROUND OF THE INVENTION

The present invention relates generally to a coupling device for detachably connecting an eyepiece of an endoscope optical system with a camera lens.

Coupling devices are used to take an eyepiece of an endoscopic instrument otherwise used for viewing with the eye and connect it to a camera. Such a coupling device is known from DE 69 26 837 U. This device provides a ring element that can be screwed into the distal end of a lens casing. An inner ring engages into the ring element, forming a receptacle for the proximal end section of an eyepiece shaped like a truncated cone. Several radial boreholes are distributed over the periphery of the inner ring, which are each used for accommodating a locking sphere. The inner ring is enveloped by a rotatable, annular handle. The inner periphery of this handle exhibits oblong recesses that correspond to the boreholes of the inner ring, and become continuously deeper in the peripheral direction of the handle. The handle is preloaded by a spring against its rotational direction relative to the ring element. In an eyepiece not introduced in the inner ring, the locking spheres are always in their position that otherwise fixes the conical section of the eyepiece in place. In order to introduce the eyepiece into the inner ring, the handle must be turned against its preloaded spring in such a way that the locking spheres can engage into the recesses formed on the handle at their deepest location. Letting go of the handle causes it to be moved by the released spring, thereby pressing the locking spheres inward into the boreholes of the inner ring as the depth of the recesses in the handle decreases, where they then project out of the inner periphery of the inner ring, enveloping the conical section of the eyepiece, fixing it in place in this way. To release the eyepiece in the coupling device, the handle must again be turned against its preloaded spring, so that the locking spheres can again move to the outside, meaning away from the eyepiece, in the recesses formed on the handle.

BRIEF SUMMARY OF THE INVENTION

Against the above backdrop, an objective of a preferred embodiment of the present invention is to provide a coupling device for detachably connecting an eyepiece of an endoscope optical system with a camera lens that is easier to operate than coupling devices known in the art.

The objective is achieved by means of a coupling device having a receptacle for an eyepiece, attachment means for securing the eyepiece in the receptacle, and a manually activated handle arranged on the outside for releasing the attachment. Advantageous further developments of this coupling device may be gleaned from the following description, as well as the drawings. According to a preferred embodiment of the present invention, the features indicated in the dependent claims can here be used both separately and combined in a technologically sensible way to further configure the solution according to a preferred embodiment of the present invention as described in the independent claim(s).

The coupling device according to a preferred embodiment of the present invention for detachably connecting an eyepiece of an endoscope optical system with a camera lens exhibits a receptacle for the eyepiece. The receptacle here serves to accommodate a proximal end section of the eyepiece that expands like a truncated cone, which commonly is also referred to as an eyepiece funnel. In addition, the coupling device according to a preferred embodiment of the present invention exhibits attachment means for securing the eyepiece in the receptacle, and a manually activated handle arranged on the outside of the coupling device for releasing the attachment.

According to a preferred embodiment of the present invention, the attachment means are controlled by the eyepiece in a way that, while the eyepiece is being introduced into the receptacle, the eyepiece is automatically secured in the receptacle. In other words, as the eyepiece is introduced into the receptacle of the coupling device according to a preferred embodiment of the present invention, a latching means need advantageously no longer be released beforehand, as had previously been required in prior art. For example, the attachment means are actuated by direct contact between the eyepiece and suitable control means, which are operatively linked with the attachment means, in such a way as to fix the eyepiece in place inside the receptacle, without any additional activation being needed on the coupling device.

In the coupling device according to a preferred embodiment of the present invention, the handle can advantageously only be manually activated to release the attachment, i.e., it only has to be activated when the eyepiece secured in the receptacle of the coupling device is to be detached from the coupling device. The handle is best arranged on an area on the outside of the coupling device that is especially easy to access by the user of the coupling device.

The handle for releasing the eyepiece can preferably be moved against spring resistance. As a consequence, the handle is preferably designed as a slider. The sliding direction of the handle relative to the eyepiece can basically be as desired. However, it is especially advantageous to have a configuration in which the sliding direction of the handle for releasing the eyepiece coincides with the direction in which the eyepiece is introduced into the receptacle. As a rule, any such motion by the handle is spontaneously or intuitively taken into account, since this motion would also cause the eyepiece to be separated from the coupling device, even if the eyepiece is not secured in the receptacle.

In the coupling device according to a preferred embodiment of the present invention, the eyepiece advantageously activates the attachment means via control means provided for this purpose. The receptacle can advantageously accommodate a movable, preferably spring preloaded control element, which is movably coupled with an attachment element to fix the eyepiece in place inside the receptacle. The control element is best arranged in the receptacle in such a way as to come into contact with the eyepiece as the eyepiece is introduced into the receptacle, moving it against its preloaded spring, wherein this motion is imparted to the attachment element in a way that creates a non-positive connection and/or preferably a positive connection between the attachment element and eyepiece, thereby fixing the eyepiece in place inside the receptacle.

To establish a movable coupling with the attachment element, the control element can be linked with the attachment element by gearing means. It is preferably provided for realizing a simpler structural design of the coupling device that an assembly forms both the control element and attachment element. Accordingly, the motion of the eyepiece during its introduction in this configuration is imparted directly to the attachment element via a portion of the assembly that comprises the control element, so that the attachment element is moved into a position in which it fixes the eyepiece in place.

In order to keep the eyepiece fixed in place inside the receptacle, the handle can best be used to lock the attachment element into this position securing the eyepiece in the receptacle. To this end, the handle can be coupled with a spring, and, once the attachment element has fixed the eyepiece in place, moved into a position that prevents the attachment element from moving by releasing this spring, meaning automatically and without manual activation.

The handle can preferably be shifted against a spring force in order to detach the eyepiece in the receptacle of the coupling device according to the invention. The handle is best fixed in the position that releases the eyepiece, in which the handle is preloaded by the spring. Preferably provided to fix the handle in place is the attachment element, which when the eyepiece is being released, is advantageously moved from the position securing the eyepiece into a position that releases the eyepiece, and holds the handle in place against force exerted by the spring in the latter position.

The coupling device advantageously exhibits an angled lever with two lever arms, wherein the lever can be pivoted around an axis arranged in the area where the two lever arms intersect. In addition, this configuration provides that a first lever arm extends at least partially into the receptacle, and a second lever arm aligned essentially perpendicular to the first lever arm forms the attachment element. In this configuration, the first lever arm forms the control element, and the second lever arm forms the attachment element for fixing the eyepiece in place inside the receptacle.

The lever is preferably pivoted to the receptacle. The first lever arm forming the control element best extends into the receptacle at an end of the receptacle that faces away from the introduction opening for introducing the eyepiece and preferably comprises a stop for the eyepiece, and there can be contacted by the eyepiece for actuating the second lever arm forming the activating element. The lever can here be pivoted to the receptacle in such a way that the second lever arm comprising the attachment element can be pivoted into the receptacle through an opening in the receptacle for securing the eyepiece, and be pivoted radially out of the receptacle from the eyepiece to release the latter.

The lever is preferably preloaded by means of a spring bracket. This spring bracket, which consists of a spiral spring element, is advantageously arranged in such a way that the eyepiece introduced into the receptacle against the force applied by the spring acts essentially perpendicular to its longitudinal expansion. After the eyepiece has been detached by activating the handle, the spring bracket is released, which causes the lever to move back to a position where the lever arm forming the control element at least partially extends into the receptacle, and the lever comprising the attachment element to move out of the inside of the receptacle, so that it does not impede access by an eyepiece to be introduced into the receptacle.

In order to secure the eyepiece in the receptacle, the lever arm forming the attachment element can advantageously exhibit a projection, which positively envelops the eyepiece funnel of the eyepiece in an attached position. For this purpose, the projection can essentially be aligned perpendicular to the longitudinal extension of the second lever arm. The projection can preferably be designed in such a way as to flatly abut the conically expanding region of the eyepiece funnel.

A second projection is preferably formed next to this projection on the lever arm comprising the attachment element, on the side facing away from the projection. This second projection advantageously abuts an interior side of the handle facing the attachment element with the attachment element in the position that fixes the eyepiece in place, thereby locking the attachment element in this position.

It is further advantageous that the second projection of the second lever arm comprising the attachment element is provided for engaging into a recess formed on the handle. This recess is best formed on the end of the handle opposite the direction of movement during eyepiece detachment. If the handle for detaching the eyepiece is moved against a force exerted by the spring, the projection can enter into the recess and secure the handle in place against the acting force of the spring, like a hook.

In another preferred further development of the coupling device according to a preferred embodiment of the present invention, three levers preferably spaced apart from each other at an angular distance of 120° can be arranged on the connecting section. This is advantageous in that the lever arms of the lever comprising the attachment elements of the eyepiece can be used to center an eyepiece situated in the receptacle similarly to a three-point guide, in such a way that the optical axis of the eyepiece coincides with the optical axis of the camera lens.

BRIEF DESCRIPTION OF THE SEVERAL
VIEWS OF THE DRAWINGS

The foregoing summary, as well as the following detailed description of the present invention, will be better understood when read in conjunction with the appended drawings. For the purpose of illustrating the present invention, there are shown in the drawings an embodiment which is presently preferred. It should be understood, however, that the invention is not limited to the precise arrangements and instrumentalities shown. In the drawings:

FIG. 3 is a side view of the coupling device according to FIG. 1, taken along the section line of FIG. 1, and FIG. 4 is a sectional view of the coupling device according to FIG. 1, in the sectional view according to FIG. 3 with the eyepiece introduced.

DETAILED DESCRIPTION OF THE INVENTION

Figure 1:
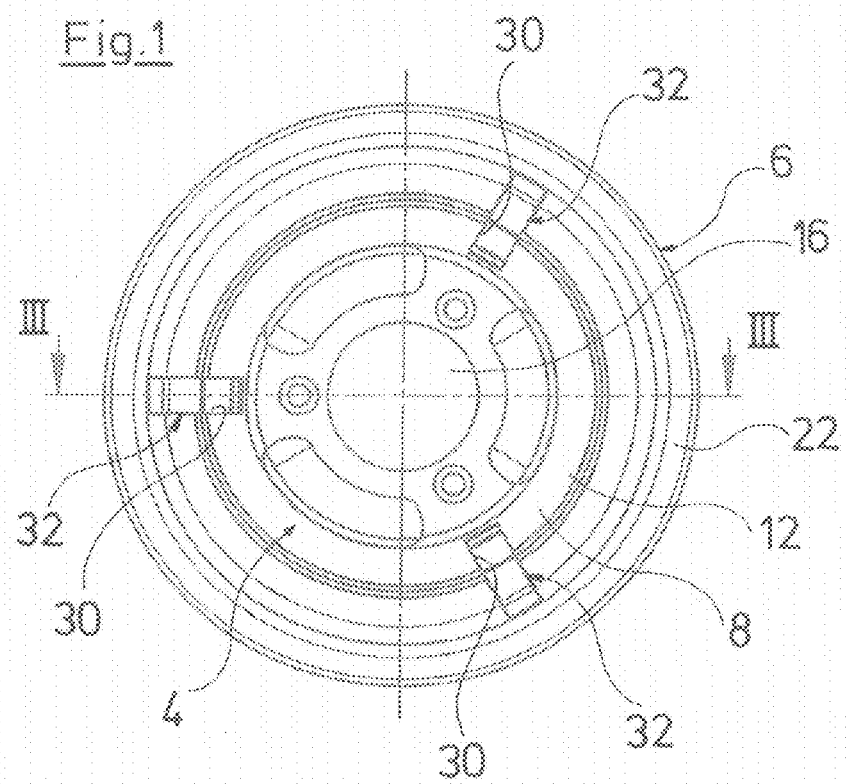
FIG. 1 is a diagrammatic top view of a coupling device according to a preferred embodiment of the present invention in a direction in which an eyepiece is introduced.
Figure 2:
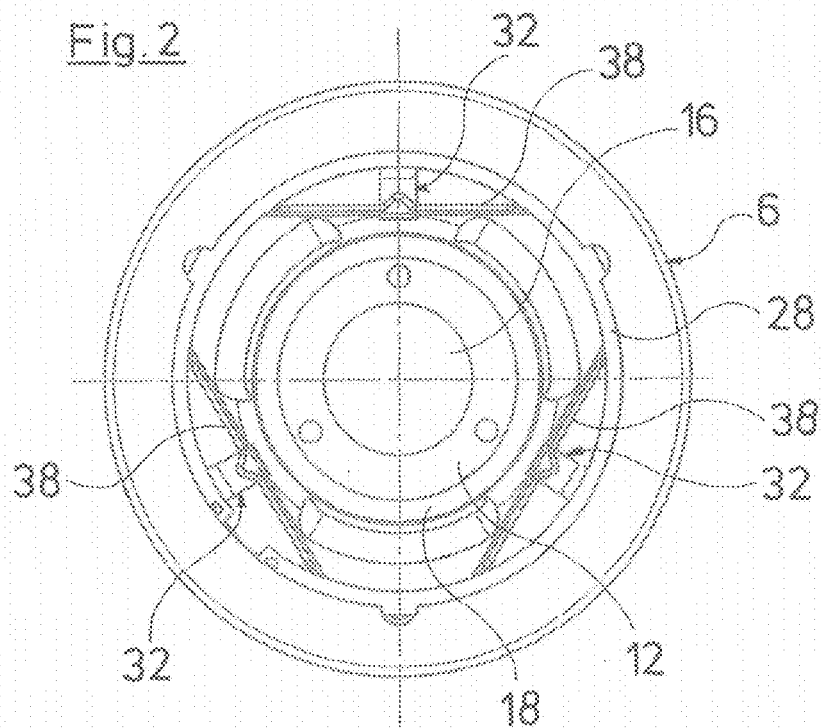
FIG. 2 is a top view of the coupling device according to FIG. 1 opposite the direction in which the eyepiece is introduced.

Certain terminology is used in the following description for convenience only and is not limiting. The words "inwardly" and "outwardly" refer to directions toward and away from, respectively, the geometric center of the device, and designated parts thereof, in accordance with the present invention. Unless specifically set forth herein, the terms "a," "an" and "the" are not limited to one element, but instead should be read as meaning "at least one." The terminology includes the words noted above, derivatives thereof and words of similar import.

The essential components of the depicted coupling device for detachably connecting an eyepiece 2 (denoted by the dashed lines in FIG. 4) of an endoscope optical system with a camera lens (not shown) include a receptacle 4 for the eyepiece 2 and a handle 6, which can be used to loosen an attachment of the eyepiece 2 in the receptacle 4.

In the receptacle 4, a hollow cylindrical section 8 with an inner diameter corresponding with the largest outer diameter of an eyepiece funnel 10 of the ocular system 2 forms a receiving space for the eyepiece funnel 10. The section 8 is open at one end for introducing the eyepiece 2. The other end of the section 8 has an annular collar 12 aligned radially inward, and an annular collar 14 aligned radially outward. The collar 12 forms a contact surface for an eyepiece 2 introduced into the receptacle 4. An opening formed by the collar 12 exhibits a diameter that essentially corresponds to the diameter of the viewing lens of the eyepiece 2.

Another hollow cylindrical section 18 of the receptacle 4 adjoins the side of the collar 12 facing away from the opening for introducing the eyepiece 2. This section 18 is coaxially aligned to the section 8 of the receptacle 4. The section 18 is used to secure the receptacle 4 to a camera lens, and together with the opening formed on the collar 12 of the section 8 yields an optical channel from the eyepiece 2 to the camera lens. For purposes of attachment to the camera lens, the outer jacket surface of the section 18 has a thread corresponding to a female thread formed at the distal end of the camera lens casing, so that the receptacle 4 can be screwed onto the camera lens. The inner diameter of the section 18 essentially corresponds to the diameter of a distal lens of the camera lens.

The handle 6 forms a hollow cylindrical interior space. The receptacle 4 is arranged concentrically to the handle 6 in this interior space, wherein the receptacle is almost completely taken up by the handle 6. An annular collar 20 directed radially inward is formed on the end of the handle 6 facing the opening for introducing the eyepiece 2 of the receptacle 4. At the end of the handle 6 facing away from the latter, the handle 6 exhibits a flange-like expansion 22 directed radially outward, which comprises a handle limit for a person using the handle 6.

The diameter of the opening of the handle 6 formed by the collar 20 corresponds with the outer diameter of the section 8 of the receptacle 4, wherein the collar 14 formed on the section 8 overlaps the collar 20 formed on the handle 6 in a radial direction. The internal side of the collar 20 of the handle 6 serves as a support for helical springs 24 standing upright at that location as depicted in FIGS. 3 and 4. The collar 14 formed on the section 8 of the receptacle 4 abuts the ends of the helical springs 24 facing away from the collar 20 of the handle 6. A continuous groove 26 is incorporated on the inner periphery of the handle 6 in the area of its end facing away from the collar 20.

This groove 26 is used to accommodate a snap ring 28. The snap ring 28 preferably overlaps the collar 14 formed on the section 8 of the receptacle 4 in a radial direction, and prevents the receptacle 4 from falling out of the interior of the handle 6.

Three openings 30 are distributed around the periphery of the section 8 at an angular distance of 120° from each other. The openings 30 each continuously extend from a radially outer region of the collar 12 over the entire length of the jacket surface of the hollow cylindrical area of the section 8, and form access openings inside the section 8. Each of the openings 30 is used to accommodate a lever 32, which is mounted in the opening 30 so that it can pivot around a swiveling axis A in the area of the collar 12.

Each lever 32 is angled, and exhibits two lever arms 34 and 36 aligned essentially perpendicular to each other, wherein the lever arms 34 are arranged essentially in the openings 30 in the region of the collar 12, and the lever arms 36 are essentially arranged in the openings 30 in the region of the jacket surface of the section 8. As shown in FIG. 3, the lever arm 34 of each lever 32 partially reaches inside the section 8 when no eyepiece 2 is introduced in the section 8 of the receptacle 4, while the lever arms 36 do not extend into the section 8. The levers 32 are each held in this position by a spring bracket 38. To this end, the individual spring brackets 38 are preferably secured to the receptacle 4 in such a way that they come to abut the side of the lever arms 34 facing away from the section 8 of the receptacle essentially transversely to the lever arms 34, where they exert a compressive force on the lever 32.

The ends of the lever arms 36 are spherically expanded, wherein they form a first projection 40 that points essentially transverse to the longitudinal expansion of the respective lever arm 36 in the direction of the inside of the section 8, and a second projection 42, which is aligned essentially opposite the projection 40. The projection 42 forms a respective angular transition to the remaining lever arm 36.

Provided on the handle 6 proceeding from the collar 20 formed there at an angular distance of 120° corresponding to the position of the lever 32 on the receptacle 4 are grooves 44, which extend radially over the entire width of the collar 20, and then on the jacket surface of the handle 6 in its longitudinal direction.

The coupling device functions as follows:

As shown in FIG. 3, the spring brackets 38 press the levers 32 into a position with the eyepiece 2 not introduced into the receptacle 4 in which the lever arms 34 partially project inside the section 8 in the area of the collar 12 of the section 8, while the lever arms 36 aligned at an inclination relative to a longitudinal axis B of the receptacle do not enter into the receptacle 8. In this position, the levers 32 are fixed in place, since the projections 42 formed on the lever arms 36 engage into the grooves 44 formed on the handle 6. In this case, the helical springs 24 are tensioned between the collar 14 of the receptacle 4 and the handle 6.

The eyepiece 2 has free access into the interior of the section 8 of the receptacle 4. If the eyepiece is introduced inside the section 8 of the receptacle 4 as depicted in FIG. 4, the eyepiece 2 comes into contact with the parts of the lever arms 34 partially projecting into the section 8 before it comes to abut the collar 12 of the section 8, and presses the levers 32 against the force applied by the spring brackets 38 into a position in which the handle 6 detaches from the lever arms 36, and the lever arms 36 are pivoted in the direction of the longitudinal axis B of the receptacle 4 in such a way that the projections 40 formed on the lever arms 36 come to abut a conically slanted region of the eyepiece funnel 10 of the eyepiece 2, thereby positively enveloping the proximal end region of the eyepiece 2. To this extent, the lever arms 34 constitute control elements for moving the lever arms 36, which in turn represent attachment means for fixing the eyepiece 2 in place inside the receptacle 4.

The movement by the lever arms 36 of the lever 32 toward the interior of the section 8 also results in the projections 42 of the lever arms 36 disengaging the grooves 44 formed on the handle 6. As a consequence, when the helical springs 24 are released, it causes the handle 6 to automatically move relative to the receptacle 4 into a position where it is situated directly outside the projections 42 of the lever arms 36, thereby preventing the lever arms 36 from moving away from the eyepiece 2, and in so doing locking the lever arms 36 in their position that fixes the eyepiece 2 in place.

In order to detach the eyepiece 2 in the receptacle 4, the handle 6 is shifted against the force applied by the helical springs 24 in the direction in which the eyepiece is introduced into the receptacle 4. This eliminates the contact between the projections 42 of the lever arms 36 and the internal side of the handle 6, causing the levers 32 to be pivoted by the preloaded spring brackets 38 in such a way that the lever arms 36 move away from the eyepiece 2 and to the outside, releasing the eyepiece 2 for removal from the receptacle 4. At the same time, the outer projections 42 formed on the lever arms again engage into the grooves 44 formed on the handle 6, and immobilize the handle 6 in this position with the helical spring 24 loaded.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A coupling device for detachably connecting an eyepiece (2) of an endoscope optical system with a camera lens, the coupling device comprising a receptacle (4) for the eyepiece (2), a lever (32) including a lever arm (34) and an attachment element (36) securing the eyepiece (2) in the receptacle (4), and a manually activated handle (6) arranged on an outside for releasing the attachment element, wherein:
the handle (6) can only be manually activated to release the attachment element, the handle (6) being shiftable against a force applied by a spring in a direction in which the eyepiece (2) is introduced into the receptacle (4), the attachment element being controlled by the eyepiece (2) so as to automatically attach the eyepiece (2) while introducing the eyepiece (2) into the receptacle (4), and
at least a portion of the attachment element contacts at least a portion of an eyepiece funnel (10) of the eyepiece (2) in an attached position, and at least a portion of the lever arm contacts a proximal end face of the eyepiece in the attached position.

2. The coupling device according to claim 1, wherein at least one spring preloaded control element is movably arranged in the receptacle (4) and movably coupled with the attachment element.

3. The coupling device according to claim 2, wherein a component (32) forms both the control element (34) and the attachment element (36).

4. The coupling device according to claim 2, wherein the attachment element is locked by the handle (6) in a position that fixes the eyepiece (2) in place in the receptacle (4).

5. The coupling device according to claim 2, wherein the attachment element can be used to fix the handle (6) into a position that releases the eyepiece (2).

6. The coupling device according to claim 5, further comprising three levers (32) spaced apart from each other at an angular distance of 120° and arranged on the receptacle (4).

7. The coupling device according to claim 2, further comprising at least one angled lever (32) with two lever arms (34, 36) being pivoted with respect to the receptacle and pivotable around an axis (A) arranged in a area where the two lever arms intersect, wherein a first lever arm (34) extending into the receptacle (4) forms the control element, and a second lever arm (36) essentially aligned perpendicular to the first lever arm (34) comprises the attachment element.

8. The coupling device according to claim 7, wherein the lever (32) is preloaded by a spring bracket (38) in an area of the lever arm (34) forming the control element.

9. The coupling device according to claim 7, wherein the lever arm (36) forming the attachment element includes a first projection (40), which positively envelops an eyepiece funnel (10) of the eyepiece (2) in the attached position.

10. The coupling device according to claim 7, wherein a second projection (42) is formed on the lever arm (36) comprising the attachment element, on a side facing away from the first projection (40).

11. The coupling device according to claim 10, wherein the second projection (42) of the second lever arm (36) comprises the attachment element and engages into a recess (44) formed on the handle (6).

* * * * *